United States Patent
Zhang et al.

(10) Patent No.: US 8,029,978 B2
(45) Date of Patent: Oct. 4, 2011

(54) PROCESSING METHOD FOR THE LONG-TERM STABILIZATION OF BIOLOGICAL RED BLOOD CELL VOLUME

(75) Inventors: Hui Zhang, Nanshan (CN); Zuyue Xu, Nanshan (CN); Mulong Liu, Nanshan (CN)

(73) Assignee: Shenzhen Mindray Bio-Medical Electronics Co., Ltd., Shenzhen (CN)

( * ) Notice: Subject to any disclaimer, the term of this patent is extended or adjusted under 35 U.S.C. 154(b) by 1191 days.

(21) Appl. No.: 11/323,702

(22) Filed: Dec. 30, 2005

(65) Prior Publication Data

US 2006/0194191 A1  Aug. 31, 2006

(30) Foreign Application Priority Data

Feb. 25, 2005  (CN) .......................... 2005 1 0033345

(51) Int. Cl.
*A01N 1/02* (2006.01)
*C01N 5/08* (2006.01)

(52) U.S. Cl. ........... 435/2; 435/372; 435/40.51; 436/10; 436/17; 436/176

(58) Field of Classification Search .................. 436/176, 436/10, 17; 435/372, 2, 40.51
See application file for complete search history.

(56) References Cited

U.S. PATENT DOCUMENTS

| | | | |
|---|---|---|---|
| 4,448,888 A * | 5/1984 | Bleile et al. | 436/67 |
| 4,704,364 A | 11/1987 | Carver et al. | |
| 4,777,139 A * | 10/1988 | Wong et al. | 436/18 |
| 5,707,801 A * | 1/1998 | Bresser et al. | 435/6 |
| 5,858,699 A * | 1/1999 | Granger et al. | 435/40.51 |
| 6,094,592 A | 7/2000 | Yorkey et al. | |
| 6,151,107 A | 11/2000 | Schöllermann et al. | |
| 6,197,539 B1 | 3/2001 | Granger et al. | |
| 6,197,540 B1 | 3/2001 | Granger et al. | |
| 6,514,763 B2 | 2/2003 | Carver et al. | |
| 7,304,415 B2 | 12/2007 | Petersen et al. | |
| 7,348,713 B2 | 3/2008 | Hashimoto | |
| 2003/0085635 A1 | 5/2003 | Davidsen | |
| 2003/0104631 A1 | 6/2003 | Carver et al. | |

FOREIGN PATENT DOCUMENTS

| | | |
|---|---|---|
| CN | 1126437 A | 7/1996 |
| CN | 94192671.0 | 7/1996 |
| CN | 1148794 A | 4/1997 |
| CN | 1149338 A | 5/1997 |

(Continued)

OTHER PUBLICATIONS

Leong. Fixation & fixatives.(2000). http://users.adam.com.au/royellis/fix.htm.*

(Continued)

*Primary Examiner* — Krishnan S Menon
*Assistant Examiner* — Rebecca M Fritchman
(74) *Attorney, Agent, or Firm* — Kory D. Christensen; Matthew S. Bethards; Stoel Rives LLP

(57) ABSTRACT

The present invention relates to a processing method for long-term stabilization of biological red blood cell volume. The red blood cells can be further used in reference materials and calibrators of a hematology analyzer. The method of the present invention comprises contacting the sample with a solution comprising a membrane-fixation reagent and an aldehyde for a processing period to terminate or slow down the red blood cell metabolism. It is provided by experiments that such process enables the volume of the red blood cells to be stable in a period over 120 days.

21 Claims, 1 Drawing Sheet

FOREIGN PATENT DOCUMENTS

| | | |
|---|---|---|
| CN | 99116350.8 | 8/2000 |
| FR | 2802449 A1 | 6/2001 |
| GB | 1 563 839 | 4/1980 |
| JP | 2003-153882 A | 5/2003 |
| JP | 2004-202190 A | 7/2004 |

OTHER PUBLICATIONS

Oxford Press. http://www.oup.com/uk/orc/bin/9780199264636/01student/video/ch18/.*

* cited by examiner

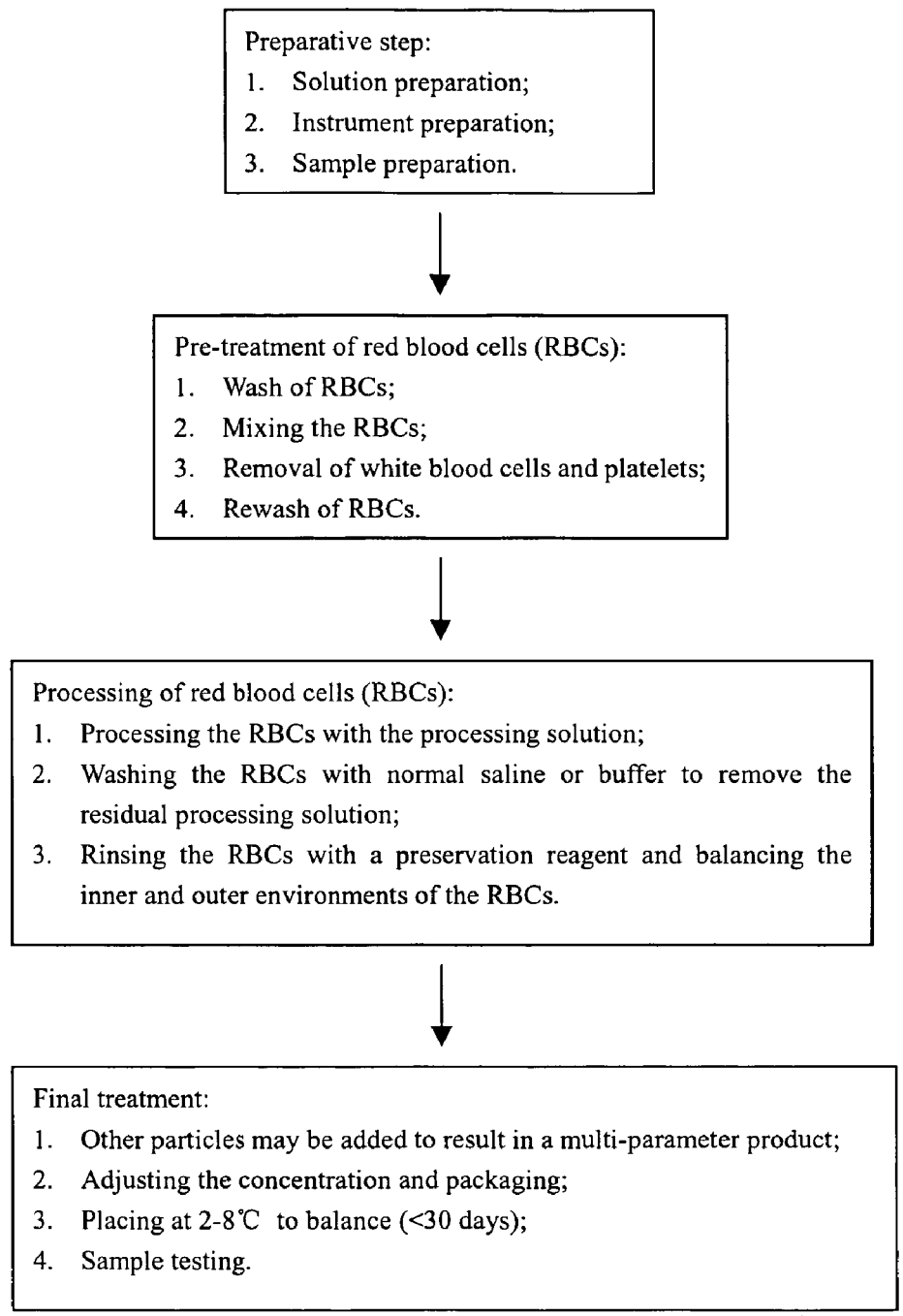

PROCESSING METHOD FOR THE LONG-TERM STABILIZATION OF BIOLOGICAL RED BLOOD CELL VOLUME

FIELD OF THE INVENTION

The present invention relates to medical formulations, particularly relating to medical formulations comprising biological red blood cells and more particularly relating to the preparation of reference materials comprising red blood cells used in blood cell analysis.

BACKGROUND OF THE INVENTION

Long-term stabilization of red blood cell (RBC) volume has great value in biological research. In a hematology analyzer, for example, both quality control and calibration need cell particles with accurate and stable volumes. Red blood cells (RBCs) are the most abundant component in biological blood and are present in, in general, 1000-fold of white blood cells. Therefore, RBCs are a key factor in setting up the volume parameter of a hematology analyzer. A hematology analyzer is able to analyze a blood sample to obtain various information from cells, e.g. cell quantity, volume, and hemoglobin, etc. Inaccurate volume parameters will result in errors in other correlated parameters, which will further lead to mistakes in clinical diagnosis. For example, inaccurate volume parameters will significantly affect specific parameters related to treatment of anaemia such as hemoglobin concentration and content in RBC. Therefore, reliable systems for quality control and calibration should be established. Successful quality control and calibration largely depend on reference materials and calibrators. Reference materials and calibrators in the prior art are generally mixtures of particles with little variation in their volumes, wherein most leukocyte-like particles and platelet-like particles, whose numbers are low, are completely fixed cell particles or plastic microspheres. Their reactivity with hemolysin, i.e. surfactant, of the hematology analyzer is not required. However, RBCs are the major component of reference materials. They must be reactive with hemolysin in order to avoid exhibiting the same physical and chemical properties as leukocyte-like particles and interfering with assays by appearing as pseudo-leukocyte particles since they are present 1000-fold over leukocyte particles. Reactivity with hemolysin is the most important difference between RBCs and leokocytes. Therefore, RBCs must fulfill the following requirements: 1. they must keep the reactivity with hemolysin of the hematology analyzer and should not interfere with identification of other parameters by appearing as pseudo-leukocyte particles; 2. they must keep a long-term stable volume and have little variation of the average volume during the shelf life of the reference materials and calibrators.

There is much literature disclosing preparation techniques of reference materials. For example, a full blood reference material for three part differential of blood cells is disclosed in Chinese patent application 99116350. A method for preparation of a hematology blood reference materials is disclosed in US patent application 20030104631. A hematology blood reference material and the preparation method thereof is disclosed in patent U.S. Pat. No. 6,514,763. And hematology control compositions for three part differential of leukocytes and methods for their preparation and use in whole blood control systems are disclosed in U.S. Pat. No. 4,704,364. Most efforts have been focused on protection of the physiological activity of RBCs and the processing of white blood cells, however, methods for RBC processing in the prior art have shown little concern with volume stabilization. Chinese patent ZL94192671 provides a method used for preparation of stable cells. However, the method mainly relates to the stability of the biological activities of cells, in particular white blood cells, rather than the stability of cell volume. Moreover, this method requires a long processing at a low temperature (4° C.) and salts of metals and aldehydes used in the process are still in the system after processing. These facts limit the application of the method.

Conventional methods for RBC processing can be categorized into two groups: processing with fixation reagents and fixation methods; and using preservation reagents for RBCs. Fixation methods usually employ aldehydes, acids, esters, ketones, and radioactivity, etc.; preservation reagents are usually reagents derived from blood or immunological materials. These techniques, if used to prepare reference materials, generally have the following defects:

(1) The fixed RBCs tend to exhibit properties of white blood cells if they are hard to break, in particular they are difficult to be dissolved completely by surfactants;
(2) The parameters, e.g, the volume, of the fixed RBCs are not stable if the cells are not fixed sufficiently, thus the cells cannot be stored for a long term;
(3) Stored RBCs with preservation reagents may sustain or partially sustain physiological activities and parameters may keep stable in a short term, but they will expire if inner or outer circumstances change.

Therefore, there are no solutions in the prior art providing a simple and rapid processing method of RBCs, which stabilizes the cell volume for a long period but keeps the cell reactivity with hemolysin of the Hematology analyzer. A processing method which enables RBCs to have little volume variation during the shelf life of the reference materials and calibrators while the cells do not interfere with measurement of other parameters is desired.

DESCRIPTION OF THE INVENTION

The present invention provides a processing method of RBCs, which enables the preparation of RBCs having little volume variation for a long period and keeping the reactivity with hemolysin of the hematology analyzer.

According to the present invention, a processing method for the long-term stabilization of biological RBC volume is provided, which comprises the step of contacting a RBC sample with a processing solution comprising a membrane-fixation reagent and an aldehyde, wherein the membrane-fixation reagent is selected from a group consisting of manganic acid or metal salts thereof, chromic acid or metal salts thereof, picric acid, and salts of cadmium, and wherein the aldehyde is selected from a group consisting of formaldehyde, paraformaldehyde, glutaraldehyde, olefine aldehyde and combinations thereof.

Preferably, the membrane-fixation reagent is potassium dichromate or cadmium chloride.

Preferably, the aldehyde is formaldehyde, glutaraldehyde, or a mixture of formaldehyde and glutaraldehyde.

Preferably, the process is carried out at room temperature and preferably the contacting is for a processing time of between 30 minutes and 3 hours.

According to the present invention, the concentration of the membrane-fixation reagent in the processing solution is 0.02%-0.5% (w/v) and the concentration of the aldehyde is 0.02%-0.3% (v/v).

Preferably, the processing solution is obtained by adding the membrane-fixation reagent and the aldehyde to a conventional nutrient-free buffer system such as citrate buffer, phosphate-buffered saline (PBS) or Tris buffer, and the final pH is between 7.1 and 8.5. In one embodiment, the buffer system comprising sodium citrate (1-10 g/L), sodium azide (1-5 g/L), potassium chloride (0.1-5 g/L), sodium sulfate (0.5-2 g/L), penicillin (0.1-2 g/L), streptomycin (0.1-2 g/L), neomycin (0.1-2 g/L), sodium chloride (1-8 g/L) and agarose or cellulose (0.2-10 mg/L) is used.

In one preferred embodiment, the processing solution comprises 0.05% (w/v) potassium dichromate and 0.08% (v/v) formaldehyde. In another preferred embodiment, the processing solution comprises 0.05% (w/v) cadmium chloride, 0.05% (v/v) formaldehyde and 0.02% (v/v) glutaraldehyde.

BRIEF DESCRIPTION OF THE FIGURE

FIG. 1 demonstrates the process of making the reference material through the processing method of the present invention.

DETAILED DESCRIPTION OF THE INVENTION

The invention provides a processing method for the long-term stabilization of biological RBC volume, which comprises contacting a RBC sample with a processing solution comprising a membrane-fixation reagent and an aldehyde, wherein the membrane-fixation reagent is selected from a group consisting of manganic acid or metal salts thereof, chromic acid or metal salts thereof, picric acid and salts of cadmium, and wherein the aldehyde is selected from a group consisting of formaldehyde, paraformaldehyde, glutaraldehyde, olefine aldehyde and combinations thereof. Preferably, the membrane-fixation reagent is potassium dichromate or cadmium chloride. Preferably, the aldehyde is formaldehyde, glutaraldehyde or the mixture of formaldehyde and glutaraldehyde. According to the invention, the biological RBCs are human RBCs, animal RBCs, or a mixed sample comprising RBCs from multiple individuals.

Not wishing to be bound by any theory, it is believed that the metabolism of RBCs contributes to the stabilization of the cells in a short period, thus keeping the RBC parameters stable. But preservation methods that supply an in vitro environment mimicking the in vivo conditions are still not available. Thus the RBC metabolism will be unbalanced after a long preservation and metabolism will have a negative effect to the preservation in such circumstances. RBC hemolysis will occur. It is therefore assumed that terminating or slowing down the RBC metabolism is favorable if a long-term stabilization of the RBC volume is required. The stable volume can be obtained through appropriate fixation and preservation techniques.

Structural analysis reveals a large amount of proteins, in addition to phospholipids, in the RBC cell membrane. A scaffold protein layer is also under the membrane. Based on these facts, the processing method of the invention tends to:

(1) terminate or slow down the RBC metabolism with chemicals; and
(2) stabilize the phospholipids with membrane-fixation reagents; and
(3) stabilize the membrane proteins with protein-fixation reagents.

According to the present invention, the processing solution is obtained by adding the membrane-fixation reagent and the aldehyde to a conventional nutrient-free buffer system such as citrate buffer, phosphate-buffered saline (PBS) or Tris buffer, and the pH is between 7.1 and 8.5.

According to the present invention, samples are processed in a neutral or basic environment with a pH of 7.1-8.5 to control the interaction between chemicals and the processing rate of RBCs to make the process mild and complete. Complete fixation should be avoided during the process to keep the reactivity with surfactants. The processing method should not be carried out under acidic conditions because the cells may be more severely hurt due to rapid reactions under such conditions.

The method according to the invention is carried out preferably at room temperature. According to the invention, the processing period should be between 30 minutes and 3 hours. The processing period should not be too long, processing more than 3 hours will not be more favorable but, in contrast, may damage some RBC samples. The processing period should be even shorter at higher temperatures.

RBCs may be in a changing period after being processed according to the method of the present invention. The changing period is generally within 30 days. Then the RBCs enter a stable period which may last more than 90 days.

The process of the invention reduces the biological diversity of samples, so different samples can be mixed to increase the total volume of the sample in order to be applied under various requirements.

The method of the present invention has a completely distinct basis compared with techniques in the prior art, as demonstrated by the following:

(1) More efforts of the prior art for RBC preservation are focused on increasing the activity of RBCs and keeping the metabolic activity, but the method of the present invention is to terminate or slow down the RBC metabolism, thus to avoid the effect of cell metabolism on RBC volume and to control the volume stability more by processing.

(2) Most conventional membrane-fixation methods do not process the phospholipids of the cell membrane due to cell damage by phospholipid processing and loss of immunological characteristics thereafter. However, the method of the invention only requires the stabilization of the cell volume, thus a phospholipid processing reagent is used to increase the membrane stability. Meantime, phospholipids can also be dissolved with surfactants resulting in cell lysis.

Conventional fixation reagents of aldehydes are used in the present invention, but with a low concentration. The major effect is to slightly fix and stabilize the protein components thus to decrease the volume change due to the change of proteins. However, the aldehydes do not counteract surfactants because of their low concentrations.

The method of the invention can be carried out simply and rapidly at room temperature, the contacting time between chemicals and cell membrane is thus shortened to maitain the integrity of the cell membrane. In contrast, fixation methods in the prior art either fix the cells completely or process the cells for a long time at a low temperature, neither of which provide good results.

The method of the invention is also favorable because the parameters of the resulted cell suspension, especially the RBC volume, can maintain their stability even if the samples are contaminated by reagents during the measurement. Such contamination is not easy to avoid.

In general, the method of the invention provides a new solution in the art to simply and rapidly carry out the long-term stabilization of RBC volume to ensure that the results of hematological analysis is trustworthy and accurate.

It should be understood by persons skilled in the art that the method of the invention can also be used in any other field without going beyond the spirit and scope of the invention to preserve cells (including platelets) or to inactivate cells. For example but not limited to: processing of white blood cells, RBCs or platelets from a non-human source; processing for stabilizing cell morphology and volume; preparing a stable cell (including platelets) suspension with a single component, wherein the suspension may be used as standard or reference material in quantitation, volume determination and the like while the normal reactivity between the hemoglobin in the RBC and the determination reagent is retained.

The method of the present invention is described below with reference to FIGURE and examples, but the invention is not limited to these specific examples.

EXAMPLE 1

This Example used a processing solution comprising potassium dichromate and formaldehyde to process the RBCs. Unless specified otherwise, all reagents were purchased from Beijing Chemical Reagents Company and were of analytical grade of purity, the carboxymethyl cellulose was obtained from ZhengXing Chemical Institute, Suzhou.

Solutions

The buffer system was as follows:

| | |
|---|---|
| Sodium citrate | 3 g |
| Sodium azide | 2 g |
| Potassium chloride | 0.1 g |
| Sodium sulfate | 1 g |
| Penicillin | 0.1 g |
| Streptomycin | 0.1 g |
| Neomycin | 0.1 g |
| Sodium chloride | 4 g |
| Carboxymethyl cellulose | 2 mg |

Distilled water was added to a final volume of 1 liter.

The osmotic pressure of the solution was adjusted to 300 mOsm with sodium chloride. It should be understood that this value is based on human RBCs. Appropriate osmotic pressure of samples from other animals may vary according to the specific animal. The pH was adjusted to 7.1 using HCl or NaOH.

Next, the processing solution of the invention was made by adding potassium dichromate and formaldehyde to the buffer system prepared as above to a final concentration of:

| | |
|---|---|
| potassium dichromate | 0.05% (w/v) |
| formaldehyde | 0.08% (v/v). |

The pH was adjusted again to 7.1 using HCl or NaOH.

Blood Sample Processing

Human blood samples were washed twice with normal saline and centrifuged for 4 minutes at 2400 rpm at room temperature using centrifuge LDJ-IIB (Shanghai Centrifuge Factory). Mixed samples from individuals should be mixed after washing to avoid agglutination due to the different blood types. White blood cells and platelets could be removed by means such as filtration or centrifugation if a pure RBC preparation was desired. Samples were subsequently washed twice with the buffer system, the supernatant was removed and the concentrated RBCs were collected for the next step.

Sample Processing After Washing

The processing solution and concentrated RBCs were mixed sufficiently, wherein the volume of the processing solution was twice that of the concentrated RBCs. The mixture was placed at room temperature for 30 minutes and washed twice with normal saline, twice with the buffer described above and twice with a preservation reagent. Finally the cells were suspended in the preservation reagent and diluted as desired before they were divided into bottles and stored at 2-8° C.

Processing Steps

As shown in FIG. 1, preparation of the reference materials comprised the steps of: preparative steps, pre-treatment of RBCs, processing of RBCs, and final treatment. The method of the invention mainly relates to processing the RBCs with the processing solution.

Results

The assay comprised determination of the change of RBC parameters in the stable period. Stability assay included determination of the change during the whole stable period and difference between bottles of a same sample and changes between results from different days before the expiration date. The assay comprised the steps of:

(1) dividing the sample after processing into bottles and storing at 2-8° C.;

(2). determining the changing period by testing the sample in a bottle everyday or every other day, the determination comprised:

a) placing the sample at room temperature for 15 minutes;

b) resuspending the cells sufficiently;

c) testing the sample on a hematology analyzer;

d) placing the sample back to 2-8° C.;

(3) starting to test other bottles when the sample entered the stable period which is around 30 days;

(4) testing the samples in the stable period as illustrated in step (2), a new bottle was opened when:

a) the sample in a bottle was not enough; or b) the RBC distribution changed significantly; or c) the RBC volume started to increase significantly.

In the example, a sample from 5 bottles was tested in 127 days.

The results of volume change with time is shown in Table 1 (statistical processing of data started from day 6 since days 1-5 were still in the changing period).

TABLE 1

| | | RBC volume ($10^{-15}$ L) | | | | | Collective |
|---|---|---|---|---|---|---|---|
| Test time | | Bottle 1 | Bottle 2 | Bottle 3 | Bottle 4 | Bottle 5 | data |
| day 1 | 10:27 | 93.1 | | | | | |
| day 2 | 9:19 | 92.8 | | | | | |
| day 3 | 8:58 | 92.3 | | | | | |
| day 4 | 9:02 | 92 | | | | | |
| day 5 | 8:45 | 93 | | | | | |
| day 6 | 10:20 | 95.3 | | | | | |
| day 7 | 11:13 | 96.1 | | | | | |
| day 8 | 8:45 | 97.1 | | | | | |
| day 9 | 9:15 | 97.1 | | | | | |
| day 10 | 8:22 | 97.1 | | | | | |

TABLE 1-continued

| Test time | | RBC volume ($10^{-15}$ L) | | | | | Collective data |
|---|---|---|---|---|---|---|---|
| | | Bottle 1 | Bottle 2 | Bottle 3 | Bottle 4 | Bottle 5 | |
| day 11 | 8:36 | 96.8 | | | | | |
| day 12 | 9:55 | 96.3 | | | | | |
| day 15 | 13:43 | 96.3 | | | | | |
| day 16 | 8:40 | 96 | | | | | |
| day 17 | 9:19 | 95.3 | | | | | |
| day 18 | 8:59 | 95.5 | | | | | |
| day 19 | 8:19 | 95.2 | | | | | |
| day 22 | 8:44 | 95.9 | 97 | | | | |
| day 23 | 8:44 | 95.8 | 96.9 | | | | |
| day 25 | 14:34 | 96 | 96.9 | | | | |
| day 26 | 9:09 | 95.7 | 96.5 | | | | |
| day 28 | 12:04 | 95.6 | 96.3 | | | | |
| day 30 | 8:27 | 95.6 | 95.8 | | | | |
| day 32 | 8:55 | 96.4 | 96.7 | | | | |
| day 36 | 8:39 | 96.3 | 96.3 | 97.1 | | | |
| day 37 | 8:41 | 95.9 | 95.7 | 97 | | | |
| day 39 | 8:56 | | 95.6 | 96.7 | | | |
| day 40 | 10:46 | | 96.3 | 97.8 | | | |
| day 42 | 11:15 | | 95.9 | 96.9 | | | |
| day 43 | 8:47 | | 95.7 | 96.6 | | | |
| day 45 | 18:25 | | 95.3 | 96.6 | | | |
| day 47 | 14:37 | | 95.5 | 95.6 | | | |
| day 50 | 11:04 | | 94.8 | 95.8 | | | |
| day 52 | 9:21 | | 94.6 | 95.6 | | | |
| day 53 | 9:34 | | 95 | 96.2 | | | |
| day 54 | 8:51 | | 95.5 | 96.5 | | | |
| day 57 | 10:33 | | 95.3 | 96.5 | | | |
| day 71 | 10:38 | | 95.1 | 96.6 | 97.7 | | |
| day 73 | 9:24 | | 94.9 | 96.5 | 97.7 | | |
| day 75 | 9:31 | | 94.8 | 96.6 | 97.5 | | |
| day 78 | 9:21 | | 95 | 96.8 | 97.5 | | |
| day 81 | 8:56 | | | 96.6 | 97 | | |
| day 89 | 9:53 | | | 96.9 | 96.5 | | |
| day 90 | 15:22 | | | 96.9 | 96.5 | 97.1 | |
| day 92 | 0:00 | | | 96.8 | 96.5 | 97.3 | |
| day 94 | 0:00 | | | 96.5 | 96.7 | 97 | |
| day 96 | 0:00 | | | | 96.3 | 97.4 | |
| day 99 | 0:00 | | | | 96.4 | 96.6 | |
| day 102 | 0:00 | | | | 97.6 | 98.5 | |
| day 106 | 0:00 | | | | 96.9 | 97.5 | |
| day 108 | 0:00 | | | | 96.6 | 97.4 | |
| day 109 | 0:00 | | | | 96.3 | 97.4 | |
| day 112 | 0:00 | | | | 95.9 | 97.3 | |
| day 114 | 0:00 | | | | | 97 | |
| day 116 | 0:00 | | | | | 96.9 | |
| day 118 | 0:00 | | | | | 96.5 | |
| day 120 | 0:00 | | | | | 96.5 | |
| day 122 | 0:00 | | | | | 96.7 | |
| day 124 | 0:00 | | | | | 96.3 | |
| day 127 | 0:00 | | | | | 96.6 | |
| Statistical results | | | | | | | |
| Average volume($10^{-15}$ L) | | 95.4077 | 95.725 | 96.5955 | 96.85 | 97.0647 | 96.396 |
| Standard deviation (SD) | | 0.59944 | 0.73854 | 0.49036 | 0.57966 | 0.53261 | 0.77341 |
| Coefficient of Variation (CV)% | | 0.6283 | 0.77152 | 0.50764 | 0.59851 | 0.54872 | 0.80233 |
| Total days | | 30.931 | 56.026 | 57.64 | 40.557 | 36.36 | 120.57 |

Coefficient of Variation (CV %) = SD/Average volume × 100%
Minimum: day 52 9:21 bottle 2 94.6 × $10^{-15}$ L
Maximum: day 102 0:00 bottle 5 98.5 × $10^{-15}$ L
Maximum difference: 3.9 × $10^{-15}$ L
Testing system: hematology analyzer BC-3000 of Shenzhen Mindray Co., LTD. Beijing
The following conclusions can be made based on Table 1:
(1) samples need a changing period, e.g. 5 days in the example, to be stable;
(2) samples change little once the stable period starts and samples are stable in a period for more than 30 days even if the bottle has been unsealed;
(3) various factors may contribute to the volume change, e.g. the stability of the hematology analyzer, stability of reagents, temperature, etc., in particular the temperature shifted from 28° C. to 16° C. during the 120 days, which suggests the change of the sample per se is even less.

The results of RBC volume differences between bottles and the volume stability at room temperature is shown in Table 2. Bottles in this assay were unsealed at the same time.

TABLE 2

| Test time | RBC volume($10^{-15}$ L) Serial number of bottles | | | | | Average volume | SD | CV between bottles (%) | control (BC-12) |
|---|---|---|---|---|---|---|---|---|---|
| | 813 # | 814 # | 815 # | 816 # | 817 # | | | | |
| day1 | 88.7 | 88.6 | 88.4 | 88.3 | 88.6 | 88.52 | 0.164 | 0.18563 | 88.6 |
| day2 | 88.3 | 88.4 | 88.4 | 88.7 | 88.5 | 88.4 | 0.187 | 0.21163 | 88.7 |
| day5 | 88.5 | 88.6 | 88.5 | 88.4 | 88.4 | 88.42 | 0.148 | 0.16775 | 88.5 |
| day6 | 88.4 | 88.7 | 88.3 | 88.4 | 88.5 | 88.46 | 0.152 | 0.17144 | 88.8 |
| day7 | 88.6 | 88.8 | 88.7 | 88.3 | 88.5 | 88.52 | 0.259 | 0.29241 | 89 |
| day8 | 88.1 | 88.6 | 88.6 | 88.4 | 88.3 | 88.4 | 0.212 | 0.23997 | 89.1 |
| day9 | 88.4 | 88.4 | 88.6 | 88.3 | 88.4 | 88.42 | 0.11 | 0.12389 | 88.7 |
| day12 | 87.8 | 88.3 | 88.5 | 88 | 87.1 | 87.96 | 0.503 | 0.57184 | 89.3 |
| | 3 values of the volume of 817 # after 12 hours at room temperature | | | | 87.9 87.8 | | | | |
| day13 | 88.1 | 88.4 | 88.1 | 88.3 | 88 | 88.525 | 0.15 | 0.17002 | 89.3 |
| | 3 values of the volume of 817 # after 24 hours at room temperature | | | | 87.7 87.9 | | | | |
| day14 | 88.1 | 88.3 | 88.5 | 88.5 | 88.1 | 88.575 | 0.171 | 0.19347 | 89.1 |
| | 3 values of the volume of 817 # after 48 hours at room temperature | | | | 88 87.9 | | | | |
| | *13 µl diluent was added to 816 #* | | | 88.5 | 88.3 | | | | |
| day15 | 88.3 | 88.5 | 88.5 | *88.7* | 88.6 | 88.425 | 0.222 | 0.25076 | 89.1 |
| day16 | 88.5 | 88.5 | 88.3 | *88.5* | 88.7 | 88.375 | 0.15 | 0.16973 | 89 |
| | *13 µl diluent was added to 816 # again* | | | 88.3 | Data in bold are for the test at room | | | | |
| day19 | 88.4 | 88.5 | 88.4 | | temperature | 88.4333 | 0.058 | 0.06529 | 89.2 |
| | *816 # at day 4* | | | 88.5 | and are not | | | | |
| day20 | 87.9 | 88.7 | 88.5 | *88.9* | taken into | 88.5 | 0.432 | 0.48819 | |
| day21 | 88 | 88.9 | 88.6 | *89.2* | account for | 88.675 | 0.512 | 0.57778 | |
| day22 | 88.3 | | 88.8 | *89.2* | CV between | 88.7667 | 0.451 | 0.50799 | |
| day30 | 88.4 | 88.8 | 89 | *89.1* | bottles. | 88.825 | 0.31 | 0.34852 | 89.5 |
| | *200 µl diluent was added to 816 #* | | | 88.8 | Data in bold italics are for | | | | |
| day31 | 88 | 88.5 | 88.7 | *88.5* | the test of | 88.425 | 0.299 | 0.3377 | 89.3 |
| day32 | 87.5 | 88.7 | 88.6 | *89.9* | contamination | 88.675 | 0.981 | 1.10637 | 89.2 |
| day33 | 87.7 | 88.5 | 88.7 | *90.5* | and are not taken into account for CV between Bottles. | 88.85 | 1.182 | 1.33011 | 89.2 |
| Average volume | 88.185 | 88.532 | 88.52 | 88.691 | 88.1421 | Collective average volume | | 88.3844 | 89.0352941 |
| SD | 0.3066 | 0.2056 | 0.2118 | 0.5783 | 0.37016 | Collective SD | | 0.29915 | 0.2827127 |
| Self CV % | 0.3476 | 0.2323 | 0.2392 | 0.6521 | 0.41996 | Collective CV % | | 0.3385 | 0.3175288 |
| Total days | 32 | 32 | 32 | 32 | 15 | | | | 32 |

Testing system: hematology analyzer BC-3000 of Shenzhen Mindray Co., LTD. Shenzhen

*Data from reference material BC-12 (from Hematronix Inc.) are for control only.

The following conclusions can be made based on Table 2:

(1) different bottles have little difference;

(2) samples can be stable for at least 48 hours at room temperature;

(3) samples processed with the method of the present invention are stable and the stability is not affected by the addition of diluent with little volume;

(4) together with data in Table 1, cells processed with the method of the invention do not exhibit differences according to different processing systems, different processing places and different processing personnel.

EXAMPLE 2

Cadmium chloride and a mixture of formaldehyde and glutaraldehyde were used to treat the RBCs.

The buffer system was the same as used in Example 1. The processing solution comprised 0.05% (w/v) cadmium chloride, 0.05% (v/v) formaldehyde and 0.02% (v/v) glutaraldehyde.

Samples were processed in the same way as in Example 1

Results

The results of RBC volume change with time is shown in Table 3

TABLE 3

| Test time | RBC volume($10^{-15}$ L) | | | | | |
|---|---|---|---|---|---|---|
| | Bottle 1 | Bottle 2 | Bottle 3 | Bottle 4 | Bottle 5 | Collective |
| day1 | 94.90 | | | | | |
| day2 | 93.50 | | | | | |
| day3 | 94.40 | | | | | |
| day5 | 95.10 | | | | | |
| day6 | 95.30 | | | | | |
| day7 | 95.00 | | | | | |
| day8 | 94.80 | | | | | |
| day9 | 94.90 | | | | | |
| day10 | 94.40 | | | | | |
| day11 | 95.60 | | | | | |
| day12 | 95.40 | | | | | |
| day13 | 95.10 | | | | | |
| day14 | 94.30 | | | | | |
| day15 | 94.40 | | | | | |
| day16 | 94.10 | | | | | |
| day7 | 93.90 | | | | | |
| day20 | 94.20 | | | | | |
| day21 | 93.70 | | | | | |
| day22 | 93.70 | | | | | |
| day23 | 93.90 | | | | | |
| day24 | 94.00 | | | | | |
| day27 | 94.10 | 94.00 | | | | |
| day28 | 94.00 | 93.70 | | | | |
| day30 | 94.40 | 94.30 | | | | |
| day31 | 94.40 | 93.80 | | | | |
| day33 | 93.80 | 93.60 | | | | |
| day35 | 93.90 | 93.20 | | | | |
| day37 | 94.80 | 93.70 | | | | |
| day41 | 94.20 | 93.70 | | | | |
| day42 | 94.20 | 93.40 | | | | |
| day44 | 93.90 | 93.80 | | | | |
| day45 | | 94.00 | | | | |
| day47 | | 93.60 | | | | |
| day48 | | 93.20 | | | | |
| day52 | | 93.20 | | | | |
| day55 | | 93.10 | | | | |
| day57 | | 92.80 | | | | |
| day58 | | 93.30 | | | | |
| day59 | | 93.60 | | | | |
| day62 | | 94.10 | | | | |
| day76 | | 94.00 | 94.30 | | | |
| day78 | | 93.60 | 94.20 | | | |
| day80 | | 93.80 | 93.80 | | | |
| day83 | | 93.80 | 94.50 | | | |
| day86 | | 93.40 | 94.20 | | | |
| day94 | | 93.80 | 94.20 | 94.70 | | |
| day95 | | | | 94.70 | | |
| day97 | | | 94.50 | 94.40 | 95.00 | |
| day99 | | | 94.20 | 94.40 | 94.70 | |
| day101 | | | | 94.20 | 94.70 | |
| day104 | | | | 94.60 | 94.40 | |
| day107 | | | | 95.50 | 95.90 | |
| day111 | | | | 95.20 | 95.60 | |
| day113 | | | | | 95.90 | |
| day114 | | | | | 95.80 | |
| day117 | | | | | 95.60 | 95.60 |
| day119 | | | | | 96.10 | 95.60 |
| day121 | | | | | | 95.70 |
| day123 | | | | | 95.30 | 95.60 |
| day125 | | | | | 95.90 | 95.70 |
| day127 | | | | | 95.60 | 95.40 |
| day129 | | | | | 96.10 | 95.50 |
| day132 | | | | | 96.70 | 96.10 |
| day134 | | | | | 96.80 | 96.50 |
| day136 | | | | | 96.50 | 96.40 |
| day139 | | | | | 97.50 | 96.80 |
| day141 | | | | | 97.50 | 96.90 |
| day143 | | | | | 97.00 | 97.30 |
| day145 | | | | | 96.50 | 96.40 |
| day147 | | | | | 96.90 | 96.10 |
| day149 | | | | | 96.60 | 97.30 |
| day153 | | | | | 97.00 | 96.90 |
| day155 | | | | | 97.00 | 97.30 |
| day156 | | | | | 97.10 | 97.40 |
| day158 | | | | | 97.50 | 97.50 |
| Average volume ($10^{-15}$ L) | 94.40 | 93.67 | 94.46 | 96.09 | 96.40 | 94.99 |
| SD | 0.54 | 0.39 | 0.45 | 0.93 | 0.71 | 1.26 |
| CV % | 0.58 | 0.41 | 0.47 | 0.96 | 0.74 | 1.32 |
| Total days | 42.98 | 71.64 | 34.56 | 63.59 | 41.00 | 156.63 |

Testing system: hematology analyzer BC-3000 of Shenzhen Mindray Co., LTD.

From Table 3, RBCs processed with cadmium chloride and a mixture of formaldehyde and glutaraldehyde exhibit stable volumes in a period of 156 days.

Persons skilled in the art should understand that substitution and amendments to the method of the present invention without deviation from the spirit of the invention fall within the scope of the present invention.

The invention claimed is:

1. A processing method for the long-term stabilization of biological red blood cell volume, comprising:
   contacting red blood cells in a blood sample with a processing solution comprising a membrane-fixation reagent and an aldehyde,
   wherein the membrane-fixation reagent is selected from a group consisting of dichromate salts, picric acid and salts of cadmium, wherein the membrane fixation reagent is added such that the concentration in the processing solution is 0.02%-0.5% (w/v), and wherein the aldehyde is selected from a group consisting of formaldehyde, paraformaldehyde, glutaraldehyde, olefine aldehyde and combinations thereof; and
   stabilizing the red blood cell volume in the blood sample with a coefficient of variation of 1.32% or less for over 30 days, excluding a changing period of the first 5 days.

2. The method according to claim 1, wherein the membrane-fixation reagent is potassium dichromate or cadmium chloride.

3. The method according to claim 1, wherein the aldehyde is formaldehyde, paraformaldehyde, or a mixture of formaldehyde and glutaraldehyde.

4. The method according to claim 1, wherein the contacting is carried out at room temperature.

5. A processing method for the long-term stabilization of biological red blood cell volume, comprising:
   contacting red blood cells in a blood sample with a processing solution comprising a membrane-fixation reagent and an aldehyde,
   wherein the membrane-fixation reagent is selected from a group consisting of dichromate salts, picric acid and salts of cadmium, and wherein the aldehyde is selected from a group consisting of formaldehyde, paraformaldehyde, glutaraldehyde, olefine aldehyde and combinations thereof, and wherein the contacting of the blood sample with the processing solution lasts for a period of between 30 minutes and 3 hours, and stabilizing the red blood cell volume in the blood sample with a coefficient of variation of 1.32% or less for over 30 days, excluding a changing period of the first 5 days.

6. The method according to claim 1, wherein the concentration of the aldehyde is 0.02%-0.3% (v/v).

7. The method according to claim 6, wherein the processing solution comprises 0.05% (w/v) potassium dichromate and 0.08% (v/v) formaldehyde.

8. The method according to claim 6, wherein the processing solution comprises 0.05% (w/v) cadmium chloride, 0.05% (v/v) formaldehyde and 0.02% (v/v) glutaraldehyde.

9. The method according to claim 1, wherein the processing solution is obtained by adding the membrane-fixation reagent and the aldehyde to a common nutrient-free buffer system such as citrate buffer, phosphate-buffered saline (PBS) and Tris buffer, and the final pH is between 7.1 and 8.5.

10. The method according to claim 9, wherein a nutrient-free buffer system comprising sodium citrate (1-10 g/L), sodium azide (1-5 g/L), potassium chloride (0.1-5 g/L), sodium sulfate (0.5-2 g/L), penicillin (0.1-2 g/L), streptomycin (0.1-2 g/L), neomycin (0.1-2 g/L), sodium chloride (1-8 g/L) and agarose or cellulose (0.2-10 mg/L) is used.

11. The method according to claim 1, wherein the biological RBCS are human RBCS, animal RBCS, or a mixed sample comprising RBCS from multiple species.

12. A processing method for the long-term stabilization of biological red blood cell volume, comprising:

removing white blood cells from a blood sample to create a red blood cell sample;

stabilizing phospholipids in membranes of red blood cells with a membrane-fixation reagent, wherein the membrane fixation reagent is selected from a group consisting of dichromate salts, picric acid and salts of cadmium; and stabilizing membrane proteins in membranes of red blood cells with a protein-fixation reagent comprising an aldehyde selected from a group consisting of formaldehyde, paraformaldehyde, glutaraldehyde, olefine aldehyde and combinations thereof;

wherein the combination of the membrane-fixation reagent and the protein-fixation reagent is capable of stabilizing the red blood cell volume in the red blood cell sample with a coefficient of variation of 1.32% or less for over 30 days, excluding a changing period of the first 5 days.

13. The method of claim 12, further comprising buffering an environment of each step of the method at a pH of between 7.1 and 8.5.

14. The method of claim 12, wherein inhibiting the metabolism of red blood cells comprises using a red blood cell nutrient-free system.

15. The method of claim 1, wherein the membrane-fixation reagent is selected from the group consisting of dichromate salts and picric acid.

16. The method of claim 1, wherein red blood cell volume is stabilized with a coefficient of variation of 1.32% or less for at least 120 days.

17. The method of claim 12, wherein red blood cell volume is stabilized with a coefficient of variation of 1.32% or less for at least 120 days.

18. The method of claim 1, wherein red blood cell volume is stabilized with a coefficient of variation of 1.32% or less for at least 150 days.

19. The method of claim 12, wherein red blood cell volume is stabilized with a coefficient of variation of 1.32% or less for at least 150 days.

20. The method of claim 1, wherein red blood cell volume is stabilized with a coefficient of variation of 1.32% or less for at least 60 days.

21. The method of claim 12, wherein red blood cell volume is stabilized with a coefficient of variation of 1.32% or less for at least 60 days.

* * * * *